United States Patent
Schanen et al.

(10) Patent No.: US 8,471,059 B2
(45) Date of Patent: Jun. 25, 2013

(54) METHOD FOR PREPARING A TRIFLUOROMETHANESULFINIC ACID SALT

(75) Inventors: Vincent Schanen, Lyons (FR); Olivier Buisine, Saint Genis Laval (FR); François Metz, Irigny (FR); Bernard Besson, Les Echets (FR)

(73) Assignee: Rhodia Operations, Aubervilliers (FR)

( * ) Notice: Subject to any disclaimer, the term of this patent is extended or adjusted under 35 U.S.C. 154(b) by 365 days.

(21) Appl. No.: 12/745,196

(22) PCT Filed: Nov. 25, 2008

(86) PCT No.: PCT/EP2008/066162
§ 371 (c)(1),
(2), (4) Date: Oct. 26, 2010

(87) PCT Pub. No.: WO2009/068534
PCT Pub. Date: Jun. 4, 2009

(65) Prior Publication Data
US 2011/0034724 A1 Feb. 10, 2011

(51) Int. Cl.
*C07C 313/04* (2006.01)
(52) U.S. Cl.
USPC .......................................... 562/125; 562/113
(58) Field of Classification Search
USPC ................................. 562/113, 125
See application file for complete search history.

(56) References Cited

U.S. PATENT DOCUMENTS 6,770,776 B2 * 8/2004 Janin et al. ............... 560/153
2001/0031891 A1 10/2001 Goto et al.

FOREIGN PATENT DOCUMENTS

EP 0735023 10/1996
WO WO 0149659 7/2001

OTHER PUBLICATIONS

Harzdorf, et al.; Über Perlluralkansulfinsäuren; Liebigs Annaien Der Chemie, No. 1. Feb. 22, 1973, pp. 33-39, XP002491378.

* cited by examiner

*Primary Examiner* — Peter G O Sullivan
(74) *Attorney, Agent, or Firm* — Hunton & Williams, LLP

(57) ABSTRACT

The present invention relates to a method for preparing a salt of trifluoromethanesulphinic acid termed "triflinic acid". More specifically, the invention relates to a method for preparing a highly pure triflinic acid salt. The method of the invention for preparing a highly pure triflinic acid salt, starting from an aqueous mixture comprising the latter combined with a trifluoroacetic acid salt and saline impurities resulting from the method for preparing same, is characterized in that said mixture is subjected to the following operations: —first controlled acidification such that the trifluoroacetic acid salt is essentially released in the acid form thereof, the majority of the triflinic acid remaining in a salified form, —optional separation of the salts originating from the acid having been used for the acidification and recovery of an aqueous phase, —separation of the trifluoroacetic acid from the separated aqueous phase comprising the alkaline salt of triflinic acid, trifluoroacetic acid, triflinic acid and the excess strong acid, therefore resulting in an aqueous phase depleted of trifluoroacetic acid but comprising the alkaline salt of triflinic acid, —recovery of the alkaline salt of triflinic acid from the aqueous phase.

38 Claims, No Drawings

METHOD FOR PREPARING A TRIFLUOROMETHANESULFINIC ACID SALT

CROSS-REFERENCE TO RELATED APPLICATIONS

This application is the U.S. National Phase of International Application Number PCT/EP2008/066162 filed on Nov. 25, 2008, which claims priority to French Application No. FR 07/08282, filed Nov. 27, 2007.

A subject matter of the present invention is a process for the preparation of a trifluoromethanesulfinic acid salt.

The invention is targeted at the preparation of a trifluoromethanesulfinic acid salt of high purity and more particularly an alkali metal salt of trifluoromethanesulfinic acid.

Trifluoromethanesulfinic acid, commonly known as "triflinic acid", or else its salified forms are products used in numerous fields (plant protection, pharmaceutical or other).

One of the routes for the synthesis of said acid described in EP 0 735 023 consists in reacting trifluoroacetic acid, at least partially salified by an organic or inorganic cation, with sulfur dioxide in a polar organic solvent and heating the resulting mixture at a temperature of between 100° C. and 200° C. for a period of time of between 30 min and 20 hours.

The relative amounts of trifluoroacetic acid and sulfur dioxide are such that the ratio of the number of sulfur atoms per mole of trifluoroacetic acid is between 1 and 10, advantageously in the vicinity of 2.

At the end of the reaction, trifluoroacetic acid, triflinic acid in the saline form, preferably in the form of an alkali metal salt, preferably the sodium or potassium salt, and the organic solvent are obtained.

Fluoride or sulfate salts, generally in the form of an alkali metal salt, preferably the sodium or potassium salt, are also coproduced during the reaction. These salts formed are known as "saline impurities" in the continuation of the present text.

Diluting is carried out by addition of water and then the polar organic solvent is extracted with an appropriate organic solvent, for example a chlorinated aliphatic hydrocarbon.

The organic and aqueous phases are separated.

There is generally obtained an aqueous solution having a solids content of 10 to 40% by weight comprising:
- from 5 to 35% by weight of a triflinic acid salt, preferably an alkali metal salt,
- from 5 to 35% by weight of a trifluoroacetic acid salt, preferably an alkali metal salt,
- from 0.5 to 2% by weight of saline impurities.

Said aqueous solution preferably comprises from 15 to 20% by weight of a triflinic acid salt, from 10 to 15% by weight of a trifluoroacetic acid salt and from 0.5 to 2% by weight of saline impurities.

The object of the present invention is to provide a triflinic acid salt of high purity starting from an aqueous phase comprising a triflinic acid salt in combination with a trifluoroacetic acid salt and saline impurities resulting from its process of preparation.

The term "high purity" is understood to mean, in the present text, a triflinic acid salt having a purity of greater than or equal to 90%, preferably of greater than or equal to 95%.

Thus, a subject matter of the present invention is a process for the preparation of a triflinic acid salt of high purity starting from an aqueous mixture comprising it in combination with a trifluoroacetic acid salt and saline impurities resulting from its process of preparation, characterized in that said mixture is subjected to the following operations:

- first acidification, controlled in such a way that essentially the salt of the trifluoroacetic acid is released in its acid form, the majority of the triflinic acid remaining in a salified form,
- optional separation of the salts originating from the acid which has been used for the acidification and recovery of an aqueous phase,
- separation of the trifluoroacetic acid from the separated aqueous phase comprising the alkali metal salt of the triflinic acid, the trifluoroacetic acid, the triflinic acid and the excess strong acid, then resulting in an aqueous phase impoverished in trifluoroacetic acid but comprising the alkali metal salt of the triflinic acid,
- recovery of the alkali metal salt of the triflinic acid from the aqueous phase.

According to a first embodiment of the invention, the separation of the trifluoroacetic acid concomitantly with the triflinic acid can be carried out by treatment of the separated aqueous phase, comprising the alkali metal salt of the triflinic acid, the trifluoroacetic acid, the triflinic acid and the excess strong acid, using an organic solvent capable of extracting the organic acids formed (trifluoroacetic acid, triflinic acid), followed by the separation of the organic and aqueous phases.

According to another alternative form of the process of the invention, the trifluoroacetic acid is separated by distillation from the aqueous phase comprising the alkali metal salt of the triflinic acid, the trifluoroacetic acid, the triflinic acid and the excess strong acid.

The process of the invention is based on the fact that the salt of the trifluoroacetic acid is separated from the salt of the triflinic acid by carrying out a controlled acidification of the aqueous mixture comprising them in such a way that essentially the salt of the trifluoroacetic acid is converted to an acid form, the majority of the triflinic acid remaining in a salified form.

In accordance with the process of the invention, the controlled acidification of the starting aqueous mixture is carried out in a first stage.

The acidification is carried out using a strong acid having a $pk_a$ of less than or equal to 1.

The $pk_a$ is defined as the ionic dissociation constant of the acid/base pair when water is used as solvent.

The choice is made of a strong acid which advantageously does not exhibit an oxidizing nature. Thus, nitric acid is not preferred. Sulfuric acid, hydrochloric acid or phosphoric acid is more preferably resorted to.

Sulfuric acid is preferably chosen.

The amount of strong acid employed is such that the ratio of the number of moles of acid, expressed as $H^+$ ions, to the number of moles of the trifluoroacetic acid salt varies between 1 and 3, preferably between 1 and 2.

A concentrated solution of strong acid is advantageously resorted to.

Use is more particularly made of the commercial forms of acids.

Mention may in particular be made of the 95 or 98% by weight sulfuric acid solutions, the 37% by weight hydrochloric acid solution or the 95-100% by weight phosphoric acid solutions.

Use may also be made of hydrochloric acid in the gaseous form or of oleums which correspond to sulfuric acid charged with sulfur trioxide $SO_3$, the concentration of which can vary between 10 and 60% by weight. Oleums comprising 20, 40 or 60% by weight of $SO_3$ are commercially available.

The acidification operation is advantageously carried out at a temperature of between 0° C. and 60° C., preferably between 0° C. and 10° C.

At the end of the acid treatment, an aqueous solution or suspension is collected which comprises the salt of the triflinic acid, the trifluoroacetic acid, the triflinic acid, the excess strong acid, the salts formed subsequent to the acidification and the acid forms corresponding to the saline impurities.

Generally, this suspension comprises from 10 to 20% by weight of the salt of the triflinic acid, from 5 to 20% by weight of trifluoroacetic acid and from 30 to 80% of water.

According to an alternative form of the invention, it is possible to add, to the aqueous solution or suspension obtained, a compound capable of trapping hydrofluoric acid, for example boric acid or silica, for example at a content of 1% by weight.

Before carrying out the extraction of the organic acids, it is possible but not essential to carry out a separation of the solids present in the aqueous suspension (salts, silica and the like) according to conventional solid/liquid separation techniques, preferably by filtration.

According to a first alternative form of the process of the invention, the trifluoroacetic acid is separated concomitantly with the triflinic acid by liquid/liquid extraction using an organic solvent.

To this end, the separated aqueous phase obtained, comprising the alkali metal salt of the triflinic acid, the trifluoroacetic acid, the triflinic acid and the excess strong acid, is treated using an organic solvent exhibiting an atom carrying a free electron pair, in order to extract, into an organic phase, the organic acids formed (trifluoroacetic acid, triflinic acid).

Mention may be made, as examples of such solvents, of solvents of amine or ether type.

Preferred examples of solvents of amine type are the amines having from 2 to 20 carbon atoms and mention may very particularly be made of primary amines, such as ethylamine, propylamine or isopropylamine, or tertiary amines, such as triethylamine or tris(3,6-dioxa-heptyl)amine, sold under the name TDA-1.

Mention may in particular be made, as regards solvents of ether type suitable for the process of the invention, of aliphatic, cycloaliphatic or aromatic ethers and more particularly methyl tert-butyl ether, dipentyl ether, diisopentyl ether, ethylene glycol dimethyl ether (or 1,2-dimethoxyethane), diethylene glycol dimethyl ether (or 1,5-dimethoxy-3-oxapentane), anisole, veratrole or cyclic ethers, for example dioxane or tetrahydrofuran.

The preferred solvents are methyl tert-butyl ether and diisopropyl ether.

The amount of solvent employed generally represents from 100 to 1000% of the weight of the aqueous phase, preferably from 100 to 500%.

At the end of the extraction, two phases are obtained: an aqueous phase, comprising the salt of the triflinic acid and optionally salts formed subsequent to the acidification (for example $KHSO_4$, when sulfuric acid is employed for the acidification), and an organic phase, comprising the organic solvent, the organic acids formed and optionally the excess of the acid used in the acidification.

In a following stage, the aqueous and organic phases are separated according to conventional settling or centrifuging techniques and the alkali metal salt of the triflinic acid is recovered from the separated aqueous phase.

According to a second alternative form of the process of the invention, the trifluoroacetic acid is separated by distillation from the separated aqueous phase.

The abovementioned aqueous phase, comprising the salt of the triflinic acid, the trifluoroacetic acid, the triflinic acid, the excess strong acid, the salts formed subsequent to the acidification and the acid forms corresponding to the saline impurities, is introduced into a distillation column and the trifluoroacetic acid and optionally water are removed at the distillation top and the salt of the triflinic acid, accompanied by the excess strong acid, the salts of the strong acids, in particular those originating from the acidification, and water, is recovered at the distillation bottom.

The distillation is carried out at a temperature in the reboiler of between 60° C. and 90° C. under a pressure ranging from 700 mbar to 10 mbar.

It is carried out in a conventional distillation apparatus.

A person skilled in the art is fully in a position to choose the means to be employed according to the compounds to be separated.

A reminder will simply be made of the following. The size (in particular the diameter) of the distillation columns depends on the circulating stream and on the internal pressure. They will thus be designed mainly according to the flow rate of the mixture to be treated. The internal parameter, which is the number of theoretical stages, is determined in particular by the purity of the starting compound and the purity of the product which has to be obtained at the distillation top.

It will be specified that the columns can be packed indifferently with plates or with stacked packing, as is fully known to a person skilled in the art.

The plant being established, a person skilled in the art adjusts the operating parameters of the column.

Thus, the distillation column can advantageously but not limitingly be a column having the following specifications:
  number of theoretical stages: from 1 to 10, preferably from 1 to 5,
  reflux ratio R of between 1 and 20, preferably between 5 and 10.

A distillation concentrate comprising the salt of the triflinic acid is recovered at the column bottom and a gas phase, composed of the trifluoroacetic acid optionally accompanied by water, is recovered at the column top.

The gas phase is cooled and is converted into the liquid form by cooling to a temperature, for example, of between −20° C. and 20° C., preferably of between −10° C. and 10° C.

This operation is carried out by passing through a condenser which is a conventional device, for example a tube heat exchanger fed with water or with a fluid maintained at a temperature in the vicinity of the cooling temperature chosen.

The choice is advantageously made, in carrying out the distillation operation, of equipment capable of withstanding the corrosion brought about by the compounds to be separated.

To this end, the choice is made of materials advantageously of the enamel steels.

A distillation concentrate is recovered which comprises the alkali metal salt of the triflinic acid and the saline impurities.

The alkali metal salt of the triflinic acid present in the aqueous phase obtained subsequent to liquid/liquid extraction or in the distillation concentrate can be recovered according to various alternative embodiments.

According to a first embodiment of the invention, the alkali metal salt of the triflinic acid present in the aqueous phase obtained subsequent to liquid/liquid extraction or in the distillation concentrate is recovered by subjecting them to the following operations:
  second acidification of the recovered phase in such a way that the salt of the triflinic acid is released in its acid form,
  treatment of the separated aqueous phase comprising essentially the triflinic acid using an organic solvent capable of extracting the triflinic acid, separation of the organic and aqueous phases,
treatment of the organic phase using a basic aqueous solution in such a way that the salt of the triflinic acid is collected in the aqueous phase,
removal of the water by distillation and replacement with an organic solvent in order to obtain the salt of the triflinic acid in an organic solution,
precipitation of the salt of the triflinic acid using a nonsolvent or by crystallization,
separation and recovery of said salt.

The aqueous phase collected is subjected to a second acid treatment as described above with the only difference that a much greater amount of acid is employed. The salt of the triflinic acid is thus released in its acid form.

The amount of strong acid employed is such that the ratio of the number of moles of acid, expressed as $H^+$ ions, to the number of moles of salt of the triflinic acid varies between 1 and 10 and preferably between 2 and 4.

In a following stage, the triflinic acid is extracted using an organic solvent. A basic organic solvent as described above is preferably resorted to. The choice is preferably made of solvents of ether type and more preferably still methyl tert-butyl ether, diisopropyl ether or veratrole.

At the end of the extraction, two phases are obtained: an aqueous phase, comprising the salts formed subsequent to the acidification, and an organic phase, comprising the organic solvent, the triflinic acid and the residual strong acid.

In a following stage, the aqueous and organic phases are separated according to conventional settling or centrifuging techniques.

The organic phase collected is subjected to a basic treatment in order to salify the triflinic acid obtained.

To this end, commercial basic solutions are preferably resorted to. Mention may be made, as examples, of aqueous solutions of alkali metal hydroxides, preferably sodium hydroxide or potassium hydroxide, advantageously having a concentration of 10 to 50% by weight.

The amount of base added is such that a pH of between 5 and 9, preferably in the vicinity of 7, is obtained.

At the end of the basic treatment, two phases are obtained: an aqueous phase, comprising the salt of the triflinic acid, and an organic phase, comprising the organic solvent.

In a following stage, the aqueous and organic phases are separated according to conventional settling or centrifuging techniques.

The separated aqueous phase is subjected to a distillation operation, which makes it possible to remove the water at the distillation top and to collect, at the distillation bottom, essentially the salt of the triflinic acid and less than 2 to 10% by weight of water.

To this end, the distillation is carried out at a reboiler temperature which, for safety reasons, is maintained at less than 90° C.

The distillation is preferably carried out at a temperature in the reboiler of between 60° C. and 90° C. under a pressure of between 1 mbar and 600 mbar.

In a following stage, the traces of water are removed by treatment of the distillation concentrate using an organic solvent.

Two imperatives govern the choice of the solvent: it must be miscible with water, that is to say form a homogeneous mixture with water, and it must also dissolve the salt of the triflinic acid obtained.

Mention may in particular be made, as examples of organic solvents meeting these requirements, of the solvents of alcohol type.

It is preferable to resort to alcohols having a low carbon condensation, preferably less than 6 carbon atoms and more preferably still less than 4 carbon atoms.

Mention may be made, as more specific examples of alcohols suitable for the implementation of the invention, of, inter alia, methanol, ethanol, n-propanol, isopropanol, butanol, isobutanol, tert-butanol, amyl alcohol, cyclopentanol, cyclohexanol or dibenzyl alcohol.

Isopropanol is the alcohol preferably employed.

Mention may be made, as other solvents capable of being used, of solvents of ketone type, such as, for example, methyl isobutyl ketone, or methyl ethyl ketone, or solvents of ester type, such as, for example, ethyl acetate or butyl acetate.

A single phase is obtained which comprises the solvent, the salt of the triflinic acid and the water.

A filtration can optionally be carried out if insoluble salts originating from the strong acid used for the acidification extracted by the organic solvent are present.

The salt of the triflinic acid is recovered from the phase comprising the solvent, the salt of the triflinic acid and the water according to two preferred embodiments: either by precipitation by treatment of said phase using a nonsolvent or by crystallization.

According to the first embodiment, the salt of the triflinic acid is precipitated by treatment of the phase obtained using a nonsolvent.

Mention may in particular be made, as examples of nonsolvents, of aliphatic, cycloaliphatic or aromatic hydrocarbons and more particularly hexane, cyclohexane, methylcyclohexane, petroleum fractions of petroleum ether type; aromatic hydrocarbons, such as in particular toluene, xylenes, cumene, mesitylene or petroleum fractions composed of mixtures of alkylbenzenes, in particular fractions of Solvesso type.

As regards halogenated aliphatic or aromatic hydrocarbons, mention may more particularly be made of dichloromethane, 1,2-dichloroethane, monochlorobenzene or dichlorobenzene.

The salt of the triflinic acid is separated, preferably by filtration, and an organic phase is recovered which comprises the solvent of alcohol type and the nonsolvent.

One or more washing operations, carried out using the nonsolvent as defined above, is/are optionally carried out.

Drying is optionally carried out at a temperature advantageously of between 20° C. and 80° C., preferably of between 30° C. and 50° C.

The drying is preferably carried out under a reduced pressure preferably chosen between 0.1 and 200 mbar.

The drying is carried out under a controlled atmosphere of inert gases, such as nitrogen or rare gases, for example argon.

The purified salt of the triflinic acid is obtained.

According to the other embodiment of the invention, the salt of the triflinic acid is recovered by crystallization from the phase comprising the solvent, the salt of the triflinic acid and the water.

To this end, it is crystallized by carrying out cooling of said phase, for example between 0° C. and 40° C.

The crystallized salt of the triflinic acid is separated, preferably by filtration, and dried as described above.

According to a second embodiment of the invention, the alkali metal salt of the triflinic acid present in the aqueous phase is recovered by subjecting the aqueous phase to the following operations:
concentration of the separated aqueous phase,
treatment of the separated aqueous phase, comprising essentially the salt of the triflinic acid, the salts formed subsequent to the acidification and the acid forms corresponding to the saline impurities, using an organic solvent capable of extracting the salt of the triflinic acid, separation of the suspended salts, separation of the organic and aqueous phases, recovery of the salt of the triflinic acid from the separated organic phase.

The aqueous phase comprising the salt of the triflinic acid which is collected subsequent to the separation of the organic and aqueous phases is subjected to a concentration operation.

According to one characteristic of the process of the invention, the reaction medium can be concentrated so as to increase the concentration of the salt of the triflinic acid in such a way that between 2 and 30%, preferably between 5 and 20%, of water is present in the concentrated solution obtained.

Another embodiment for concentrating the reaction medium consists in carrying out the distillation of the amount of a portion of the water in order to achieve, in the reaction medium, the desired concentration of triflinic acid in the salified form.

The distillation can be carried out at atmospheric pressure at a temperature of 100° C.

The distillation can also be carried out under a pressure slightly less than atmospheric pressure, for example of between 5 mbar and 600 mbar, and at a temperature of less than 100° C. In general, the pressure is chosen in order to have a distillation temperature lying between 40° C. and 90° C.

Another embodiment consists in carrying out an entrainment by injection of a fluid, for example steam or inert gas, in particular nitrogen.

From a practical viewpoint, the concentration operations as well as the distillation operations described above can be carried out in an evaporator. Use may be made of those which are available commercially and mention may be made, inter alia, of wiped film evaporators or falling film evaporators of LUWA® type.

The invention does not rule out the use of other concentrating techniques, such as ultrafiltration or reverse osmosis.

In a following stage, the salt of the triflinic acid is extracted using an organic solvent. A polar aprotic organic solvent which is insoluble or partially soluble in water (for example less than 5% by weight) is preferably resorted to.

The choice is preferably made of solvents of alcohol type, such as methanol, ethanol, propanol, isopropanol, butanol, isobutanol, tert-butanol, amyl alcohol, cyclopentanol, cyclohexanol or dibenzyl alcohol, or of ketone type, such as methyl isobutyl ketone or methyl ethyl ketone, or of ester type, such as methyl, ethyl, propyl, isopropyl, butyl, isobutyl, tert-butyl or isoamyl acetate. This list of solvents is under no circumstances limiting.

At the end of the extraction, an organic phase, comprising essentially the salt of the triflinic acid, and an aqueous phase, comprising the salts formed subsequent to the acidification and the acid forms corresponding to the saline impurities, are obtained.

The aqueous and organic phases are separated.

The organic phase is concentrated by evaporation of the organic solvent in such a way that the salt of the triflinic acid precipitates.

To this end, the organic solution obtained is brought to a temperature of less than 90° C., preferably between 30° C. and 60° C.

The solution is allowed to cool to ambient temperature: the salt of the triflinic acid precipitates.

The salt of the triflinic acid is separated according to conventional solid/liquid separation techniques, preferably by filtration.

One or more washing operations, carried out using the solvent used above of alcohol, ketone or ester type or using a nonsolvent which can be chosen from those listed above, can be carried out.

In a following stage, the salt of triflinic acid obtained can be subjected to a drying operation which can be carried out as indicated above for the first alternative embodiment of the invention.

The salt of the triflinic acid is obtained in a purified form.

According to a third embodiment of the invention, the alkali metal salt of the triflinic acid present in the aqueous phase is recovered by subjecting the aqueous phase to the following operations:

removal of the water present in the aqueous phase comprising the alkali metal salt of the triflinic acid, addition of an organic solvent in order to dissolve the salt of the triflinic acid, recovery of the salt of the triflinic acid from the separated organic phase.

In accordance with this embodiment, the water can be removed by simple distillation of the water carried out at a temperature of 100° C. or at a lower temperature when the pressure is chosen below the atmospheric pressure but it is preferable to remove the water by azeotropic distillation by virtue of the use of a solvent capable of forming an azeotrope with the water and also capable of dissolving the salt of the triflinic acid.

Mention may in particular be made, as solvents which are entirely well suited, of solvents of alcohol type and more particularly methanol, ethanol, propanols, butanols, amyl alcohol, cyclopentanol, cyclohexanol or dibenzyl alcohol. Butanols are preferred among these alcohols.

The distillation is generally carried out advantageously at a temperature in the reboiler of between 40° C. and 70° C. and under a reduced pressure of less than 1 bar and greater than 10 mbar, preferably between 15 mbar and 400 mbar.

At the end of the distillation, the salt of the triflinic acid dissolved in the organic solvent is recovered at the distillation bottom.

Said salt is recovered in a way as described above, for example by precipitation by addition of a nonsolvent or more simply by crystallization by cooling.

The salt of the triflinic acid is separated according to conventional solid/liquid separation techniques, preferably by filtration.

It can be subjected to a drying operation as described above.

The salt of the triflinic acid is obtained in a purified form.

The process of the invention is highly advantageous as it results in a salt of the triflinic acid with a high purity of greater than or equal to 90%, preferably of greater than or equal to 95% and preferentially of between 95 and 98%.

Implementation examples of the invention are given below by way of indication and without a limiting nature.

EXAMPLE 1

An aqueous solution (1.7 kg) comprising 16% by weight of potassium trifluoromethanesulfinate and comprising 15% by weight of potassium trifluoroacetate is charged to a jacketed glass reactor equipped with a central stirrer and maintained under a nitrogen atmosphere.

Concentrated 96% sulfuric acid (163 g) is added while maintaining the temperature of the reaction mass below 10° C.

A precipitate appears, which precipitate is easily removed by filtration.

1750 g of aqueous solution are thus obtained.

Four liquid/liquid extractions of the aqueous phase are carried out with 4430 g of methyl tert-butyl ether.

The organic phases obtained are discarded and the remaining aqueous phase (1440 g) is acidified with 375 g of concentrated 96% sulfuric acid.

The aqueous phase is extracted three times with 1720 g of methyl tert-butyl ether.

The organic phases are combined (w=1560 g) and the residual aqueous phase (w=1538 g) is discarded.

The preceding organic solutions are neutralized at 0° C. using 138 g of a concentrated 50% by weight potassium hydroxide solution.

At the end of the neutralization, the aqueous phase is close to neutrality.

456 g of aqueous solution are thus obtained.

This solution is concentrated under a reduced pressure of 20 mbar and a temperature of 50° C. approximately, so as to remove 241 g of water.

Isopropanol is added (320 g) and distillation is maintained under identical conditions until 521 g of organic solution are obtained.

The organic solution is run onto 1100 g of anhydrous toluene.

The precipitated solid is isolated by filtration and dried under a pressure of 10 mbar at 50° C.

184 g of potassium trifluoromethanesulfinate with a purity of 97% are obtained.

EXAMPLE 2

An aqueous solution (1.7 kg) comprising 16% by weight of potassium trifluoromethanesulfinate and 15% by weight of potassium trifluoroacetate is charged to a reactor.

Concentrated 96% sulfuric acid (163 g) is added while maintaining the temperature of the reaction mass below 10° C.

A precipitate appears, which precipitate is easily removed by filtration.

1750 g of aqueous solution are thus obtained.

Four liquid/liquid extractions of the aqueous phase are carried out with 4430 g of methyl tert-butyl ether.

The organic phases obtained are discarded and the remaining aqueous phase (1440 g) is acidified with 375 g of concentrated 96% sulfuric acid.

This aqueous phase is concentrated under a reduced pressure of 3 mbar and a temperature of 45° C., so as to distill off 186 g of water.

The concentrated aqueous solution obtained (w=353 g) is diluted in 630 g of isopropyl alcohol.

A precipitate is formed, which precipitate is removed by filtration.

778 g of a homogeneous organic solution are thus obtained.

This solution is concentrated under a reduced pressure of 20 mbar and a temperature of 40° C., so as to distill off 230 g of isopropyl alcohol.

After concentrating, the organic solution is run onto 910 g of toluene, which brings about the precipitation of the potassium trifluoromethanesulfinate.

The solid is isolated by filtration and dried at 50° C. under a pressure of 10 mbar.

175 g of dry potassium trifluoromethanesulfinate with a purity of 96% are obtained.

EXAMPLE 3

An aqueous solution (1.7 kg) comprising 16% by weight of potassium trifluoromethanesulfinate and 15% by weight of potassium trifluoroacetate is charged to a reactor.

Concentrated 96% sulfuric acid (163 g) is added while maintaining the temperature of the reaction mass below 10° C.

A precipitate appears, which precipitate is easily removed by filtration.

1750 g of aqueous solution are thus obtained.

Four liquid/liquid extractions of the aqueous phase are carried out with 4430 g of methyl tert-butyl ether.

The organic phases obtained are discarded and the remaining aqueous phase (1440 g) is acidified with 375 g of concentrated 96% sulfuric acid.

This aqueous phase is concentrated under a reduced pressure of 3 mbar and a temperature of 45° C., so as to distill off 186 g of water.

The concentrated aqueous solution obtained (w=353 g) is diluted in 630 g of isopropyl alcohol.

A precipitate is formed, which precipitate is removed by filtration.

785 g of a homogeneous organic solution are thus obtained.

This solution is concentrated under a pressure of 20 mbar and at a temperature of 40° C., so as to obtain 291 g of concentrated organic solution.

The temperature is lowered to ambient temperature and a solid crystallizes.

The latter is isolated by filtration and dried at 45° C. under a pressure of 2 mbar.

133 g of dry potassium trifluoromethanesulfinate with a purity of 96% are obtained.

EXAMPLE 4

An aqueous solution (100 g) comprising 16% by weight of potassium trifluoromethanesulfinate and 15% by weight of potassium trifluoroacetate is charged to a reactor.

Sulfuric acid (9.5 g, 0.09 mol) is added while maintaining the temperature at 10° C.

A solid appears and the latter is removed by filtration.

14.6 g of solid and 90.4 g of filtrate are obtained.

This filtrate is subsequently distilled under reduced pressure.

The temperature is brought to 70° C. under a reduced pressure of 20 mbar.

Water is added to keep the level of liquid constant in the reboiler.

A fraction weighing 92 g comprising 16% by weight of trifluoroacetic acid and 84% by weight of water is thus obtained.

Isobutanol (800 g) is added to the medium and the water is removed by azeotropic distillation under a pressure of 120 mbar, the temperature of the medium being brought to 60° C.

The fraction having a boiling point of 42° C. is isolated.

As the water is removed, a white solid appears.

The latter is removed from the medium by filtration.

12.9 g of solid are obtained.

The azeotropic distillation is halted when 774 g of distillate are obtained.

The temperature is lowered to 0° C. and a solid crystallizes.

The latter is isolated by filtration under an inert atmosphere and then sucked dry under a stream of nitrogen.

39.6 g of white solid are obtained.

The latter is dried under a pressure of 0.1 mbar at ambient temperature for 72 hours.

32.8 g of potassium trifluoromethanesulfinate having purity of 96% by weight are obtained.

What is claimed is:

1. A process for the preparation of a triflinic acid salt of high purity comprising:
adding a strong acid to an aqueous mixture comprising the triflinic acid salt, a trifluoroacetic acid salt, and saline impurities,
substantially converting the trifluoroacetic acid salt to an acid form wherein the majority of triflinic acid remains in a salified form;
optionally removing salts originating from the strong acid;
recovering an aqueous phase comprising the triflinic acid salt, trifluoroacetic acid, triflinic acid, and excess strong acid;
separating the trifluoroacetic acid from the aqueous phase and reducing the amount of trifluoroacetic acid in the aqueous phase; and
recovering the triflinic acid salt from the aqueous phase.

2. The process of claim 1, wherein the aqueous mixture comprises an aqueous solution with a solids content ranging from 10 to 40% by weight comprising:
from 5 to 35% by weight of the triflinic acid salt,
from 5 to 35% by weight of the trifluoroacetic acid salt, and
from 0.5 to 2% by weight of saline impurities.

3. The process of claim 2, wherein said aqueous solution comprises from 15 to 20% by weight of the triflinic acid salt, from 10 to 15% by weight of the trifluoroacetic acid salt, and from 0.5 to 2% by weight of saline impurities.

4. The process of claim 1, wherein the strong acid comprises sulfuric, hydrochloric, or phosphoric acid, an oleum, or gaseous hydrochloric acid.

5. The process of claim 4, comprising adding the strong acid in an amount such that the ratio of the number of moles of acid, expressed as $H^+$ ions, to the number of moles of the trifluoroacetic acid salt ranges from 1 to 3.

6. The process of claim 4, wherein the strong acid comprises a concentrated solution of strong acid.

7. The process of claim 4, wherein, after the addition of the strong acid, an aqueous solution or suspension is collected comprising the triflinic acid salt, the trifluoroacetic acid, the triflinic acid, the excess strong acid, salts formed subsequent to the addition of the strong acid, and acid forms of the saline impurities.

8. The process of claim 7, wherein the solution or suspension comprises from 10 to 20% by weight of the triflinic acid salt, from 5 to 20% by weight of the trifluoroacetic acid, and from 30 to 80% of water.

9. The process of claim 1, further comprising adding a compound capable of trapping hydrofluoric acid to the aqueous phase before the extraction of the orgainic acids.

10. The process of claim 1, wherein the step of separating the trifluoroacetic acid comprises separating the trifluoroacetic acid and the triflinic acid by treating the aqueous phase with an organic solvent capable of extracting the trifluoroacetic acid and triflinic acid, and then separating the resulting organic and aqueous phases.

11. The process of claim 10, wherein the organic solvent comprises an amine or an ether.

12. The process of claim 10, wherein:
the resulting aqueous phase comprises the triflinic acid salt, and optionally salts formed subsequent to the addition of the strong acid; and
the resulting organic phase comprises the organic solvent, organic acids, and optionally the excess strong acid.

13. The process of claim 1, wherein the separation of the trifluoroacetic acid comprises:
distilling the aqueous phase;
removing the trifluoroacetic acid and optionally water from the distillation top, and
recovering the triflinic acid salt, the excess strong acid, salts of the strong acid, and water from the distillation bottom.

14. The process of claim 13, wherein the distillation is carried out at a temperature ranging from 60° C. to 90° C. and under a pressure ranging from 700 mbar to 10 mbar.

15. The process of claim 13, wherein the step of recovering the triflinic acid salt from the aqueous phase or a distillation concentrate comprises:
acidifying the aqueous phase to convert the triflinic acid salt to acid form,
adding an organic solvent capable of extracting the triflinic acid to the aqueous phase,
separating the organic and aqueous phases,
treating the organic phase with a basic aqueous solution and collecting triflinic acid salt in the aqueous phase,
removing water by distillation and adding an organic solvent to yield the triflinic acid salt in an organic solution,
precipitating the triflinic acid salt with a non-solvent or by crystallization, and
recovering said triflinic acid salt.

16. The process of claim 15, wherein the aqueous phase is acidified again with a strong acid in an amount such that the ratio of the number of moles of acid, expressed as $H^+$ ions, to the number of moles of the triflinic acid salt ranges from 1 to 10.

17. The process of claim 15, comprising extracting the triflinic acid with an organic solvent comprising methyl tert-butyl ether, diisopropyl ether, veratrole, or mixtures thereof.

18. The process of claim 15, wherein two phases are obtained at the end of the extraction: an aqueous phase, comprising the salts formed subsequent to the acidification, and an organic phase, comprising the organic solvent, the triflinic acid, and the excess strong acid.

19. The process of claim 15, comprising treating the organic phase with a base to salify the triflinic acid.

20. The process of claim 19, wherein the organic phase has a pH ranging from 5 to 9 after addition of the base.

21. The process of claim 19, wherein two phases are obtained at the end of the basic treatment: an aqueous phase, comprising the triflinic acid salt, salt formed subsequent to acidification, and an organic phase comprising the organic solvent.

22. The process of claim 15, wherein the aqueous phase is distilled at a temperature ranging from 60° C. to 90° C. under a pressure ranging from 1 mbar to 600 mbar.

23. The process of claim 15, comprising treating the distillation concentrate with an organic solvent comprising an alcohol, ketone, or ester.

24. The process of claim 15, comprising precipitating the triflinic acid salt by addition of a non-solvent.

25. The process of claim 15, comprising separating the triflinic acid salt and recovering an organic phase comprising an alcohol solvent and the nonsolvent.

26. The process of claim 1, wherein the step of recovering the triflinic acid salt from the aqueous phase comprises:
concentrating the aqueous phase;
adding an organic solvent capable of extracting the triflinic acid salt to the aqueous phase comprising the triflinic acid salt, salts formed subsequent to the acidification step, and acid forms of the saline impurities;
separating the suspended salts, separating an organic phase and the aqueous phase,
recovering the triflinic acid salt from the separated organic phase.

27. The process of claim 26, comprising increasing the concentration of the triflinic acid salt such that the concentrated aqueous phase comprises water in an amount ranging from 2 to 30%.

28. The process of claim 27, comprising removing water from said aqueous phase by distillation under a pressure equal to or less than atmospheric pressure, or by injection of a steam or an inert gas fluid.

29. The process of claim 26, wherein said organic solvent comprises an alcohol, ketone, or ester.

30. The process of claim 29, wherein the extraction yields an organic phase that comprises the triflinic acid salt, and an aqueous phase that comprises salts formed subsequent to the acidification step and acid forms of the saline impurities.

31. The process of claim 30, further comprising separating the aqueous and organic phases and concentrating the organic phase by evaporation of the organic solvent to precipitate the triflinic acid salt.

32. The process of claim 1, wherein recovering the triflinic acid salt in the aqueous phase comprises:
removing the water present in the aqueous phase comprising the triflinic acid salt,
adding an organic solvent to dissolve the triflinic acid salt, and
recovering the triflinic acid salt from a separated organic phase.

33. The process of claim 32, comprising removing the water by azeotropic distillation in the presence of a solvent.

34. The process of claim 32, comprising crystallizing the triflinic acid salt by cooling.

35. The process of claim 1, comprising separating the triflinic acid salt by filtration.

36. The process of claim 1, further comprising drying said triflinic acid salt at a temperature ranging from 20° C. to 80° C. and under a pressure ranging from 0.1 to 200 mbar.

37. The process of claim 1, wherein the triflinic acid salt has a purity of greater than or equal to 90%.

38. The process of claim 1, wherein said triflinic acid salt is an alkali metal salt of triflinic acid.

* * * * *

UNITED STATES PATENT AND TRADEMARK OFFICE
CERTIFICATE OF CORRECTION

PATENT NO. : 8,471,059 B2
APPLICATION NO. : 12/745196
DATED : June 25, 2013
INVENTOR(S) : Schanen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 517 days.

Signed and Sealed this
Eighth Day of September, 2015

Michelle K. Lee
*Director of the United States Patent and Trademark Office*